United States Patent [19]

Summers et al.

[11] Patent Number: 5,431,673
[45] Date of Patent: Jul. 11, 1995

[54] DISTAL ATHERECTOMY CATHETER

[75] Inventors: David P. Summers, Spring; Gail L. Brinson, Woodlands, both of Tex.

[73] Assignee: American BioMed, Inc., The Woodlands, Tex.

[21] Appl. No.: 895,099

[22] Filed: Jun. 8, 1992

Related U.S. Application Data

[63] Continuation-in-part of Ser. No. 833,362, Feb. 10, 1992, which is a continuation of Ser. No. 383,606, Jul. 24, 1989, Pat. No. 5,087,265, which is a continuation-in-part of Ser. No. 312,737, Feb. 17, 1989, Pat. No. 4,994,067.

[51] Int. Cl.$^6$ .............................................. A61B 17/32
[52] U.S. Cl. ................................. 606/170; 606/167; 606/171
[58] Field of Search ............... 606/127, 128, 159, 167, 606/168, 170, 171, 172, 177, 179, 180

[56] References Cited

U.S. PATENT DOCUMENTS

| | | | |
|---|---|---|---|
| 4,646,738 | 3/1987 | Trott | 606/170 |
| 4,669,469 | 6/1987 | Gifford, III et al. | 606/170 X |
| 4,919,133 | 4/1990 | Chiang | 606/180 X |
| 5,092,873 | 3/1992 | Simpson et al. | 606/170 X |

FOREIGN PATENT DOCUMENTS

WO9300048  1/1991  WIPO .................. 606/170

*Primary Examiner*—Sam Rimell
*Attorney, Agent, or Firm*—Gunn & Kuffner

[57] ABSTRACT

A distal atherectomy catheter is disclosed for removing obstructions, plaque, stenosis, occlusions, or the like from an artery or coronary vessel. The catheter comprises a flexible, hollow catheter tube. A reciprocating, and rotating or oscillating cutting element is located within a cylindrical housing mounted at the distal end of the catheter tube. The cutting element is connected to a hollow, flexible drive shaft concentrically located within the catheter tube. The cutting element housing includes a side opening window or port providing access to the interior of the housing. An idler shaft journaled about the drive shaft provides a non-rotating surface adjacent the cutting element. An annular return passage is defined between the catheter tube and the flexible drive shaft providing a discharge passage communicating with external aspirating means for collection of cuttings removed by the cutting element from the artery or coronary vessel. A guide wire extends through the catheter tube and cutting element for guiding the catheter to the occluded site in a vessel. The drive cable is connected to a drive motor housed within a handle housing.

16 Claims, 4 Drawing Sheets

DISTAL ATHERECTOMY CATHETER

RELATED APPLICATIONS

This application is a continuation-in-part of U.S. patent application Ser. No. 07/833,362 filed on Feb. 10, 1992, which is a continuation of U.S. patent application Ser. No. 07/383,606, filed Jul. 24, 1989, issued under U.S. Pat. No. 5,087,265 on Feb. 11, 1992, which is an continuation-in-part of U.S. patent application Ser. No. 07/312,737 filed Feb. 17, 1989, issued under U.S. Pat. No. 4,994,067 on Feb. 19, 1991.

BACKGROUND OF THE DISCLOSURE

The present invention is directed to an atherectomy catheter, particularly, a distal atherectomy catheter for use in the distal and coronary arteries where small vessel size and tortuosity present numerous problems of access.

Many technological advancements have been made in recent years for treatment of coronary disease. Surgical bypass techniques, such as coronary artery bypass graft surgery, are routinely performed and are highly successful. While the risks of bypass surgery have been minimized through technological advancements, opening of the chest cavity is still required. This requires special surgical skills and equipment which are not readily available in many areas. For many patients, a bypass operation may not be indicated and therefore various surgical techniques have been devised to treat occlusive coronary artery diseases of such patients. For example, various prior art devices have been developed for removing and/or compressing atherosclerotic plaque, thromboses, stenosis, occlusion, clots, embolic material, etc. from veins, arteries and the like.

One such device is disclosed in applicant's co-pending U.S. patent application Ser. No. 07/833,362 filed Feb. 10, 1992, which disclosure is incorporated by reference herein. In applicant's application, removal of occlusive material is accomplished by a reciprocal rotary cutter head mounted at the distal end of a catheter tube for excising occlusive material blocking the coronary vessel.

While the apparatus of applicant's application has been successfully shown to remove occlusive material in laboratory tests, enhanced and more efficient removal of occlusive material may be achieved with the improved apparatus described herein. One feature which is important to the acceptability of a distal atherectomy catheter by the medical community is the efficiency and speed with which the lumen of an artery or the like may be unblocked to provide normal blood flow.

U.S. Pat. No. 4,650,466 (Luther) discloses an angioplasty device comprising a woven tube of metal or plastic fibers and a retraction stylet that are attached at one end of the catheter tube for insertion into a vein, artery, and the like for the removal of plaque and similar materials. One or more guide wires are attached to the woven tube for rotation and manipulation inside the artery. The woven tube is placed within the artery and expanded to contact the interior, plaque coated, wall of the artery. Movement of the expanded woven tube abrades the plaque from the arterial wall to form particles which are trapped within the woven tubes. The trapped plaque particles are removed with the angioplasty device upon its removal from the artery of the patient.

Other prior art devices include catheters fitted with an inflatable balloon for compressing occlusive materials such as plaque against the vessel wall. U.S. Pat. No. 4,273,128 (Lary) discloses a coronary cutting and dilating instrument for treatment of stenotic and occlusive coronary artery disease. The device disclosed therein includes a cutting and dilating instrument having one or more radially extending knife blades at a forward end thereof for making the coronary incision and an inflatable balloon for dilating the stenotic artery zone immediately after the incision.

Other angioplasty devices include a catheter having a motor driven cutting head mounted at its distal end. The cutting head is connected to the drive motor via a flexible drive shaft extending through the catheter. Extremely high rotational cutting head speeds have been achieved, in the range of 50,000-300,000 rpm, by these motor driven cutter heads. Various problems, however, have been associated with the use of the balloon tipped catheters and high speed cutting heads. The balloon catheter is expanded by injection of pressurized fluid into the balloon to expand it against the wall of the artery. Some problems which have been reported include the vessel dissection, perforation, rupture, conversion of a stenosis to an occlusion, and embolization. Furthermore, angioplasty devices utilizing balloons do not remove the plaque from the arterial wall but simply compress the plaque against the wall of the vessel. Thus, the stenosis or occlusion frequently reoccur requiring further treatment.

Atherectomy devices utilizing a motor driven high speed cutting head include a number of disadvantages. Heat dissipation and vibration is a problem. The path of the occlusion in an artery is often a tortuous path and therefore the lengthy flexible drive shaft connected to the cutter head must traverse a number of bends or curves. Consequently, as the flexible drive shaft rotates, it contacts the inner wall of the catheter resulting in localized heating and vibrations due to the frictional contact. This, of course, is very uncomfortable for the patient and may result in spasm, weakening or perforation of the vessel along the route of the catheter.

It is therefore one advantage of the present invention to provide an improved atherectomy catheter having a reciprocal rotary cutter head at the distal end thereof rotated at a relatively low speed in the range of 2,000 rpm to enhance patient comfort.

One notable feature of the invention to provide an atherectomy catheter for traversing the small and tortuous vasculature of the heart while having the ability is to bore through a total obstruction and excise a hemispherical or circumferential section from the lumen of the vessel and entrap the excised section within a containment housing.

It is yet another object of the invention to provide an atherectomy catheter for progressively opening the lumen of a vessel, entrapping and discharging the excised obstructive material into a containment housing or discharge passage of the catheter until the entire obstruction has been removed leaving a smooth fissure and flap-free enlarged internal vessel diameter.

SUMMARY OF THE INVENTION

A distal atherectomy catheter is disclosed for removing obstructions, plaque, stenosis, occlusions, or the like from an artery or coronary vessel. The catheter comprises a flexible, hollow catheter tube. A reciprocating, and rotating or oscillating cutting element is located within a cylindrical housing mounted at the distal end of the catheter tube. The cutting element is connected to a hollow, flexible drive shaft concentrically located within the catheter tube. The cutting element housing includes a side opening window or port providing access to the interior of the housing. An idler shaft journaled about the drive shaft provides a non-rotating surface adjacent the cutting element. An annular return passage is defined between the catheter tube and the flexible drive shaft providing a discharge passage communicating with external aspirating means for collection of cuttings removed by the cutting element from the artery or coronary vessel. A guide wire extends through the catheter tube and cutting element for guiding the catheter to the occluded site in a vessel. The drive cable is connected to a drive motor housed within a handle housing.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
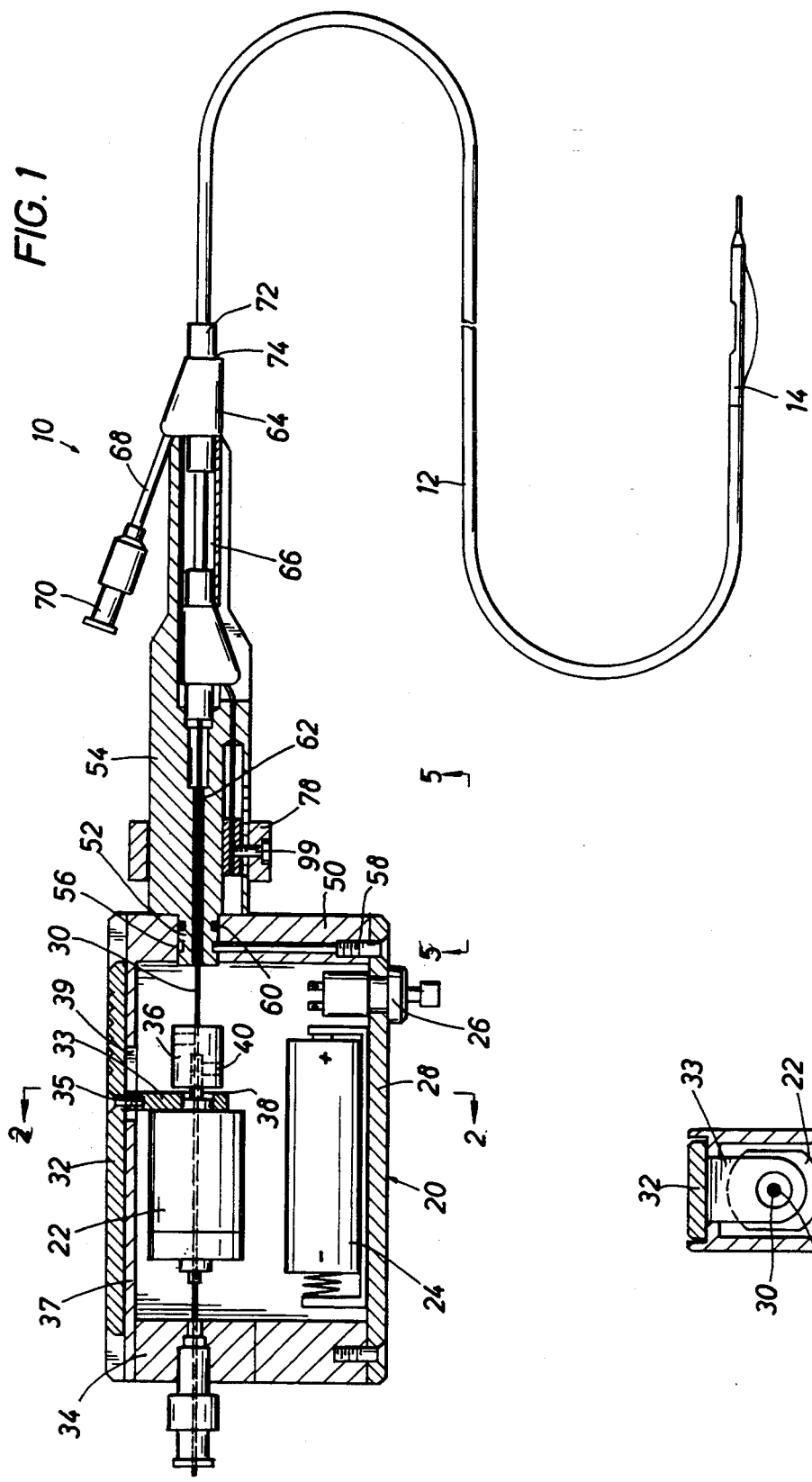
FIG. 1 is a partial sectional view of the atherectomy catheter of the invention.
Figure 2:
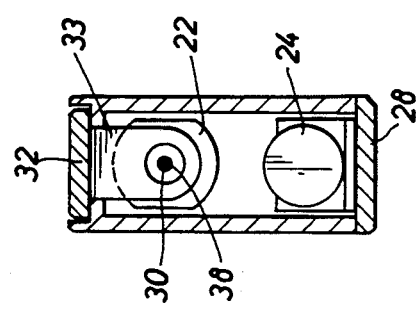
FIG. 2 is a sectional view of the invention taken along line 2—2 of FIG. 1.

Referring first to FIG. 1, the distal atherectomy catheter of the invention is generally identified by the reference numeral 10. The catheter 10 of the invention comprises a flexible outer catheter 12 which may be several feet in length. A cutter element housing 14 is threadably mounted or otherwise secured to the distal or forward end of the catheter tube 12. The proximal end of the catheter tube 12 is connected to a hand-held drive motor assembly generally identified by the reference numeral 20.

The motor assembly 20 includes a motor 22, a battery or storage cell 24 and an on-off switch 26 housed within a substantially rectangular housing 28. The motor 22, battery 24 and switch 26 are securely retained within the housing 28 and are electrically connected to provide sufficient power to operate the catheter 10. A drive shaft 30 extends axially from the motor 22. The drive shaft 30 extends through the motor 22 and is supported by a bushing 34 defining the rear wall of the housing 28 so that the drive shaft 30 rotates freely and shaft vibration is minimized. A coupling 36 connects the drive shaft 30 to the motor drive shaft 38. Set screws 40 extending into the coupling 36 fixedly securing the drive shaft 30 to the motor drive shaft 38 for establishing a rotary connection between the drive shaft 30 and the rotary drive motor 22.

The motor 22 and the drive shaft 30 are fixedly secured by the coupling 36 and reciprocate together within the housing 28. The motor 22 is connected to a slide member 32 by a downwardly depending bracket 33. The bracket 33 is threadably connected to the slide member 32 by a set screw 35 or the like. The top wall 37 of the housing 28 is provided with a slot 39, thereby enabling the motor 22 and drive shaft 30 to be jointly reciprocated within the housing 28 upon thumb actuation of the slide member 32.

The housing 28 is closed at its forward end by a wall member 50. The wall member 50 includes an opening extending therethrough for receiving the rearward extension 52 of a connector 54 which extends outwardly from the motor assembly housing 20. The extension 52 is provided with a circumferential slot 56 for receiving the tip of a screw 58 therein for locking the connector 54 to the housing 20. An O-ring seal 60 provides a fluid tight connection between the connector 54 and the housing 20.

The connector 54 includes an axial passage 62 extending therethrough. The passage 62 includes an expanded portion 66 which terminates at a Y-fitting 64 threaded or otherwise secured to the distal end of the connector 54. The axial passage 66 is in alignment with the axial passage 62, and extends through the Y-fitting 64. A passage 68 angularly branching from the axial passage 66 provides an outlet connection 70 for a cannula or syringe. The passage 68 is in fluid communication with the axial passage 66. The proximal end of the catheter tube 12 is attached to the Y-fitting 64 by a catheter retainer cap 72 threadably connected or otherwise secured to the end 74 of the Y-fitting 64.

Figure 3:
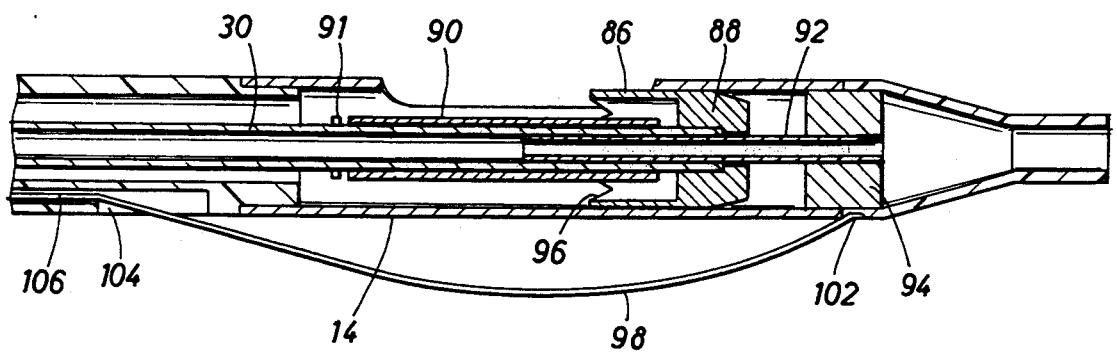
FIG. 3 is a partial sectional view of the cutting head of the invention.

Referring now to FIG. 3, the cutter head assembly of the invention is shown in greater detail. The cutter head assembly includes a cylindrical cutter housing 14 mounted to the distal end of the catheter 12. A slot or port 85 is formed in the cutter housing 14 providing access to the interior of the housing 14. The rotary cutter 86 is connected to the distal end of the hollow drive shaft 30 and located within the housing 14. The cutter 86 is substantially cylindrical in shape and partially hollow. The distal end of the drive shaft 30 is embeded or bonded to the rear wall 88 of the cutter 86. An idler shaft 90 is journaled about the drive shaft 30 adjacent to the cutter 86. The idler shaft 90 is rotationally independent from the drive shaft 30 and cutter 86; it is not rotationally connected to the drive shaft 90 or the cutter 86. The idler shaft 30 provides a non-rotating surface in the vicinity of the cutter 86 so that tissue or material cut by the cutter 86 does not wrap around the drive shaft 30 and become entwined therewith. Axial movement of the idler shaft 90 along the drift shaft 30 is limited by a retaining collar 91 mounted on the drive shaft 30. The retaining collar 91 may be bonded or welded on the drive shaft 30. Alternatively, the shaft 30 may be provided with an integral retaining shoulder to limit axial travel of the idler shaft 90.

Rotational stabilization of the cutter 86 is enhanced by a stabilizer shaft 92 which extends from a support 94 mounted at the distal end of the catheter 12. The stabilizer shaft 92 is hollow and sized to be received within the hollow drive shaft 30. The stabilizer shaft 92 is of sufficient length to provide support for the cutter 86 over it full range of movement so that reciprocal movement of the cutter 86 does not disengage or separate it from the shaft 92 when the cutter 86 is retracted within the housing 14.

The proximal end of the cutter 86 forms a serrated cutting edge 96 for removing occlusive material, such as plaque which coats the arterial wall. To aid the efficiency of the cutter 86, bowed wires 98 are provided for forcing the cutter housing 14 against the interior arterial wall of an artery or blood vessel. The bowed wires 98 are connected to the forward tip of the cutter housing 14 at 102 and extend exterior of the cutter housing 14 through an opening 104. The wires 98 extend the full length of the catheter 12 and are connected to the locator slide 78 which is manipulated back and forth to actuate the wires 98 thereby forcing the housing 14 to move laterally against the arterial wall. Alternatively, the cutter housing 14 may be laterally deflected by a balloon type deflection. Pressurized fluid may be used to expand the balloon deflector thereby laterally displacing the cutter housing 14 against the arterial wall.

Figure 5:
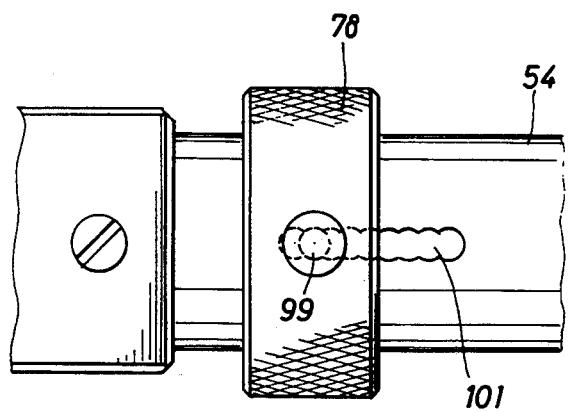
FIG. 5 is a partial bottom view showing the detente location mechanism of the invention.

Referring briefly now to FIGS. 1 and 5, it will be noted that the locator slide 78 includes a locator pin 99 cooperating with a series of detents 101 formed in the connector 54 to aid the surgeon in controlling the lateral displacement of the cutter housing 14. This permits the cutter head assembly to be correctly positioned against the wall of the artery or blood vessel. In operation, as the locater slide 78 is moved forward, the wires 98 extend into the artery and spread outwardly slightly so that the cutter head assembly is centrally located between the spread wires 98. The detent 101 enables the surgeon to determine the degree of lateral movement of the housing 14. The surgeon will hear or feel the movement of the pin 99 through the detents 101. For example, eight "clicks" may represent that the wires are fully extended and maximum lateral displacement of the housing 14 has been accomplished. Rotation of the slide knob 78 in the clockwise direction will lock the locator wires 98 in the expanded position. If the catheter is to be rotated for further positioning, the wires 98 must be completely retracted flush with the cutter housing 14 so as to avoid any damage by contact of the wires 98 with the arterial wall.

Figure 4:
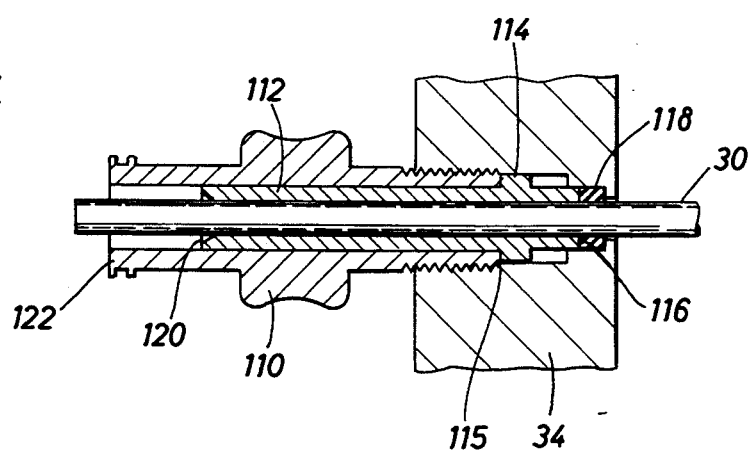
FIG. 4 is a partial sectional view showing the drive shaft seal of invention.

Referring now to FIG. 4, a syringe adaptor 110 is shown threadably engaged to the end wall 34 of the housing 20. The adaptor 110 permits a syringe (not shown in the drawings) to be connected to the catheter 10 for delivery of fluids, such as medication, through the hollow drive shaft 30 to the site of the occlusion. The adaptor 110 includes a compression sleeve 112 axially positioned within the adaptor 110.

The compression sleeve 112 includes a circumferential shoulder 114 which engages the forward end 115 of the adaptor 110, thereby preventing separation of the compression sleeve 112 from the adaptor 110 and bushing 34. The forward end 116 of the compression sleeve 112 engages an O-ring seal 118 which is journaled about the drive shaft 30. The drive shaft 30 extends through the compression sleeve 112 and the adaptor 110. The compression sleeve 112 is journaled about the drive shaft 30 and during normal use, the drive shaft 30 rotates freely within the sleeve 112. In the event delivery of medication through the catheter 12 is required, a syringe is connected to the end 122 of the adaptor 110. The forward end of the syringe extends into the adaptor 110 for engagement with the end 120 of the compression sleeve 112. Connection of the syringe to the adaptor 110, provides a compressive force on the sleeve 112, forcing it against the O-ring 118. The compressive force of the sleeve 112 expands the O-ring 118 so that it engages the shaft 30 and forms a circumferential seal therewith. Thus, the interior of the housing 20 is sealed so that medication injected through the hollow drive shaft 30 does not enter the interior of the housing 20 and come into contact with the motor 22 and battery 24. Upon disengagement of the syringe from the adaptor 110, the compressive force of the sleeve 112 on the O-ring 118 is released and the shaft 30 may again rotate freely.

Referring again to FIG. 1, the use and operation of the catheter 10 will be described. The catheter 10 is typically inserted through the femoral artery of the patient and is directed by the physician to the site of the obstruction. If a guide wire is required, the guide wire is inserted through the hollow shaft 30 and out the port 90 at the forward tip of the cutter housing 14. Alternatively, the guide wire may be inserted initially and thereafter the catheter 10 is inserted over the guide wire. Once the cutter head assembly is properly positioned, the guide wire may be removed and vacuum pump connected to the cannula 70 for creating a vacuum within the catheter 12 for aspiration of severed or excised plaque or the like as it is severed by the cutter 86. A seal in the passage 66 of the Y-fitting 64 seals off the return passage so that plaque and the like is directed to a collection vessel connected to the cannula 70.

Upon positioning the cutting head assembly of the catheter 10 for removal of an obstruction, the switch 26 is shifted to the on position so that power is applied by the battery 24 to rotate the shaft 30. If desired, prior to activating the catheter 10, the site may be irrigated with fluid and/or medication which is injected through the hollow shaft 30.

Upon actuation of the catheter 10, the shaft 30 is rotated by the motor 22. Cutting is accomplished by positioning the cutter housing 14 so that the obstructive material projects through the port 85 into the cutter housing 14, and simultaneously rotating and reciprocating the cutter 86 within the housing 14 thereby severing tissue or the like to open the blood vessel lumen. Complete opening of the lumen may be accomplished by lateral displacement of the housing 14 moving it is against the wall of the blood vessel so that the cutter 86 completely removes the obstruction in the blood vessel. Upon removal of the obstruction, the catheter 10 may be advanced further into the blood vessel or withdrawn if further treatment is not necessary.

Figure 6:
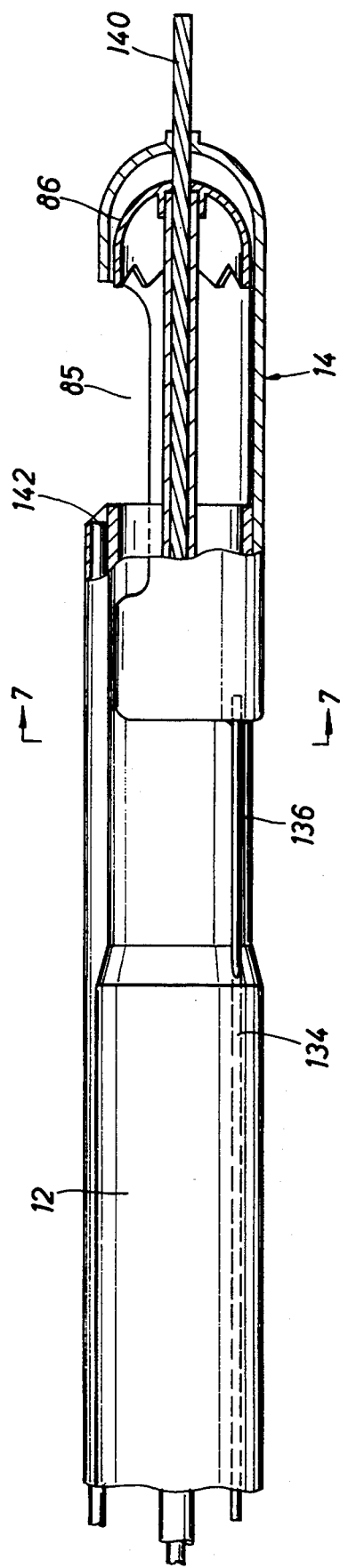
FIG. 6 is a partially broken away sectional side view of an alternate embodiment of the cutter assembly of the invention.
Figure 7:
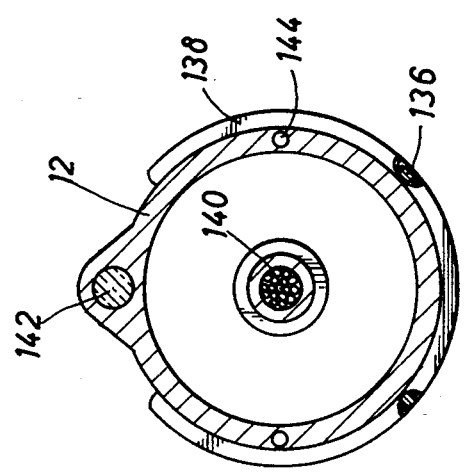
FIG. 7 is a sectional view of the cutter assembly taken along line 7—7 of FIG. 6.

Referring now to FIGS. 6 and 7, an alternate embodiment of the cutter assembly is shown. In the embodiment of FIGS. 6 and 7, the cutter housing 14 of the invention is adjustable relative to the end of the catheter 12, thereby permitting the surgeon to adjust the length of the access port 85. Adjustability of the port 85 permits the surgeon to adjust the size of the opening 85 to the size of the obstruction projecting from the wall of the blood vessel. To this end, the catheter shaft 12 is provided with a pair of slide wire lumen 134 along the length thereof. The proximal ends of the slide wires 136 are connected to the locator slide 78 mounted about the handle extension 54 and the distal end thereof is bonded or welded to a sleeve 138. The sleeve 138 defines one end of the cutter housing 14 which extends partially around the catheter 12. The sleeve 138 is profiled to enclose slightly more than half of the cylindrical body of the catheter 12 as best shown in FIG. 7. The sleeve 138 frictionally grips the catheter 12. While the sleeve 138 is depicted externally mounted about the catheter 12, it is understood that the sleeve 138 may likewise be internally mounted, if desired thereby frictionally gripping the interior wall of the catheter 12.

The slide wires 136 are bonded to the sleeve 138 and sufficiently spaced from each other to substantially eliminate rotational displacement of the cutter housing 14 relative to the catheter 12. Thus, movement of the housing 14 is limited to axial displacement along the catheter 12. The forward most end of the housing 14 is supported by a guide wire 140 extending therethrough.

A fiber optics lumen 142 extends along the catheter 12 opposite the slide actuator lumen 134. Fiber optics permit the surgeon to see the size of the obstruction and adjust the port 85 to the size of the obstruction. Thus, on a single pass the cutter 86 may be moved through the obstruction for removing a substantial portion of the obstruction; thereby reducing the number of passes of the cutter 86 required to fully open the lumen of the blood vessel. Irrigation lumen 144 terminating at the end 146 of the catheter 12 permit irrigation of the cutting site with fluid or medication as required. The irrigation lumen are in fluid communication with the passage 68 so that fluid or medication may be conventialy injection through the cannula connector 70.

Figure 8:
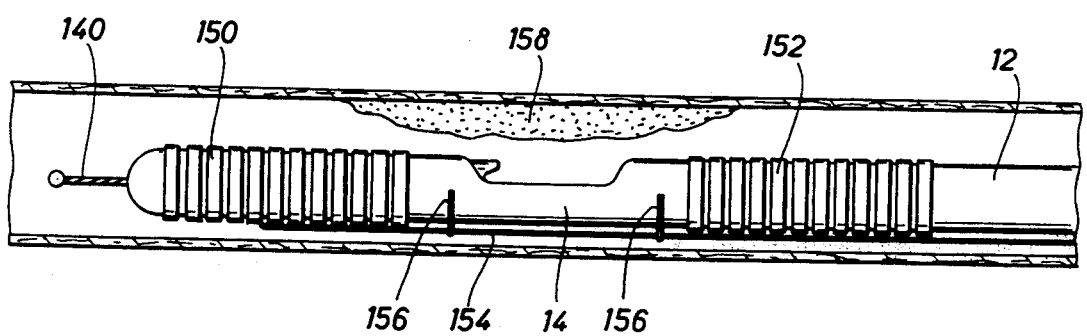
FIG. 8 is a partially broken away side view of an alternate embodiment of the invention showing an alternate means for deflecting the cutter element housing.
Figure 9:
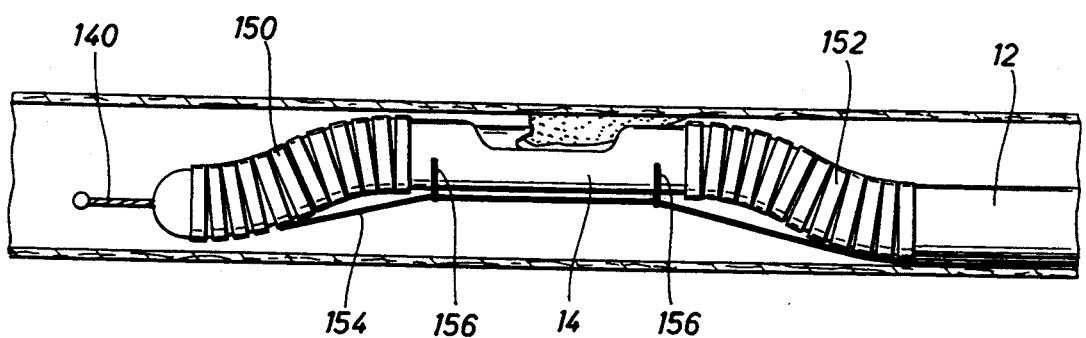
FIG. 9 is a partially broken away side view of the cutter element housing defected against the wall of an artery or coronary vessel.

Referring now to FIGS. 8 and 9, an alternate embodiment of laterally deflecting the cutter housing is shown. In the embodiment of FIGS. 8 and 9, the distal end of the catheter 12 includes segments 150 and 152 forming articulated bellows, thereby permitting the distal end of the catheter to flex in a desired direction upon tensioning a deflector wire 154. The end of the deflector wire 154 is welded to the articulated segment 150 at about the mid point thereof. The proximal end of the deflector wire 154 is connected to the slide actuator 78. A plurality of wire bridges 156 are bonded and spaced along the catheter 12 for retaining the deflector wire 154 on the catheter 12. Alternatively, the deflector wire 154 may extend through a lumen formed in the body of the catheter 12.

As previously described, during the removal of occlusive material from a blood vessel, lateral displacement of the cutter housing 14 may be desired. In the embodiment of FIGS. 8 and 9, the cutter housing 14 may be deflected toward the inner wall of the blood vessel by pulling back on the deflector wire 154. Placing the deflector wire 154 tension forces the articulated segments 150, 152 to bow outwardly, thereby deflecting the cutter housing 14 toward the obstruction 158. Once the obstruction 158 is removed, tension on the deflector wire 154 is released and the articulated segments 150, 152 relax and return the position shown in FIG. 8.

While the foregoing is directed to the preferred and illustrated embodiments of the invention, other and further embodiments of the invention may be devised without departing from the basic scope thereof, and the scope thereof is determined by the claims which follow.

What is claimed is:

1. An atherectomy catheter for removal of occlusive material in a blood vessel, tract, or cavity comprising:
   (a) a catheter tube;
   (b) a generally cylindrical cutter head assembly attached to the distal end of said catheter tube;
   (c) flexible, hollow drive means extending through said catheter tube;
   (d) a rotary cutter mounted within said cutter head assembly and connected to said flexible drive means;
   (e) power means connected to the end of said catheter tube for rotating said cutter within said cutter head assembly for excising material blocking the blood vessel;
   (f) a stabilizer shaft for guiding reciprocating movement of said rotary cutter within said cutter head assembly; and
   (g) means connected to said catheter tube for evacuating the excised material from the blood vessel through said cutter head assembly and said catheter tube.

2. The apparatus of claim 1 further including means cooperative with said cutter head assembly for moving said cutter head assembly laterally, and wherein a portion of said cutter head assembly includes an access port for occlusive material to project therethrough for removal by said rotary cutter.

3. The apparatus of claim 1 including deflector means for laterally deflecting said cutter head assembly against the occlusive material blocking the blood vessel.

4. The apparatus of claim 1 wherein said cutter head assembly has an elongate, generally cylindrical housing and includes opening means therein for admitting occlusive material into the interior of said housing, and wherein said rotary cutter cuts occlusive materials into particles sufficiently small for aspiration through said catheter tube.

5. The apparatus of claim 1 wherein said cutter head assembly comprises an elongate cylindrical housing, and including resilient means mounted thereon for urging said housing laterally toward the blood vessel wall.

6. The apparatus of claim 5 wherein said resilient means comprises a pair of bendable wires protruding from said housing, said wires forming long bows having a curvature exposed for contact and having bow ends recessed from contact against the vessel.

7. The apparatus of claim 6 including detent means for indicating the degree of extension of said wires.

8. The apparatus of claim 7 wherein said wires extend on one side of said housing diametrically opposite an access window formed in said housing.

9. The apparatus of claim 8 wherein said rotary cutter has rearwardly facing cutting means for cutting material obstructing the blood vessel.

10. The apparatus of claim 1 wherein said cutter head assembly includes an idler sleeve journaled about said flexible drive means adjacent said rotary cutter.

11. The apparatus of claim 3 wherein said deflector means comprises articulated segments forming the distal end of said catheter tube, said articulated segments being located adjacent each end of said cutter head assembly.

12. The apparatus of claim 11 including a deflector wire connecting said articulated segments to slide actuator means, wherein said cutter head assembly is deflected laterally upon placing said deflector wire in tension.

13. Apparatus for removal of unwanted or occlusive body material in a vessel, cavity or other region of the body wherein entry is via an elongate catheter, comprising:
   (a) an elongate hollow catheter tube;
   (b) a cutting head assembly attached to an end of said catheter tube and comprising:
      (1) an elongate housing defining said assembly;
      (2) an access port formed in said housing, said port being positioned to admit obstructive material into said housing;
   (c) rotatable cutting means mounted in said housing and having a cutting edge for cutting obstructive material;
   (d) power means mounted within a motor assembly housing, said power means connected to an end of said catheter tube;
   (e) hollow, drive shaft means extending through said catheter tube operatively connected to said power means;
   (f) a stabilizer shaft for guiding reciprocating movement of said rotatable cutting means within said cutter head assembly;
   (g) means positioning said cutting means in said housing for reciprocating movement to thereby enable cutting of obstructive material; and
   (h) a syringe adaptor mounted on said motor assembly housing, said syringe adaptor including seal means for sealing said motor assembly housing from fluid intrusion.

14. The apparatus of claim 13 wherein said syringe adaptor includes a compression sleeve journaled about said drive shaft means, said compression sleeve selectively engaging said seal means.

15. The apparatus of claim 13 wherein said elongate housing comprises a cylindrical hollow body, and said access port encircles approximately one half the circumference thereof, and wherein said housing includes a forwardly located full circle portion of said housing and said access port is to the rear thereof.

16. The apparatus of claim 13 including means for adjusting the length of said access port to accommodate obstructive materials of various lengths.

* * * * *